(12) United States Patent
Gelman et al.

(10) Patent No.: US 8,498,847 B2
(45) Date of Patent: Jul. 30, 2013

(54) CUT GRADING GEMSTONES, EVALUATION AND REPRESENTATION OF SYMMETRY AND PROPORTION

(75) Inventors: Pnina Gelman, Netania (IL); Shlomo Cohen, Netania (IL)

(73) Assignee: Pnina Gelman, Netania (IL)

( * ) Notice: Subject to any disclaimer, the term of this patent is extended or adjusted under 35 U.S.C. 154(b) by 577 days.

(21) Appl. No.: 12/788,548

(22) Filed: May 27, 2010

(65) Prior Publication Data
US 2010/0305924 A1 Dec. 2, 2010

Related U.S. Application Data

(60) Provisional application No. 61/182,240, filed on May 29, 2009.

(51) Int. Cl.
*G06G 7/48* (2006.01)
(52) U.S. Cl.
USPC ............................................................ 703/6
(58) Field of Classification Search
USPC ............................................................ 703/6
See application file for complete search history.

(56) References Cited

U.S. PATENT DOCUMENTS

| | | |
|---|---|---|
| 3,858,979 A | 1/1975 | Elbe |
| 3,947,120 A | 3/1976 | Bar-Issac |
| 4,647,194 A | 3/1987 | Shigetomi |
| 5,260,763 A | 11/1993 | Yamashita |
| 6,795,171 B1 | 9/2004 | Gilbertson |
| 7,193,694 B2 | 3/2007 | Underwood |
| 2006/0244946 A1* | 11/2006 | Underwood ............... 356/30 |
| 2007/0157667 A1* | 7/2007 | Maltezos et al. ............ 63/32 |
| 2007/0186918 A1* | 8/2007 | Ceulemans ............. 125/30.01 |

OTHER PUBLICATIONS

Stern N. (1975) Computer Ray Tracing in Faceted Gemstones. Master of Science Thesis, Weizmann institute of Science.
Gelman P. (1980) Polishing a Diamond to Optimal Beauty. Master of Science Thesis, Technion-Israel institute of technology, Haifa.
CGA, CutGrade Analyzer™ (2003), User's Guide.

* cited by examiner

*Primary Examiner* — Dwin M Craig

(57) ABSTRACT

A system and method for grading gemstones, based on creation and analysis of an ordered plurality of data sets, which convey information about the gemstone's cut symmetry and proportion quality and quantity. In one embodiment of the system and method, light propagation through a 3D faceted gemstone is simulated. Facets are associated with layers by rules for grouping facets. Light movement through the gemstone tagged by layer combinations along the propagation trajectory is collected, to enable rearrangement of the simulation output data in a proposed new order. An efficient analysis of the ordered plurality of data sets is provided for cut grading the symmetry and proportion of gemstones.

18 Claims, 26 Drawing Sheets

CUT GRADING GEMSTONES, EVALUATION AND REPRESENTATION OF SYMMETRY AND PROPORTION

RELATED APPLICATION

This application claims the benefit of U.S. Provisional Application No. 61/182,240, filed 29 May 2009

BACKGROUND OF THE INVENTION

The striking beauty of any cut and polished gemstone emanates from its inherent physical and optical properties together with a cutter's ability to maximize these properties.

For decades, great effort and research has been invested to accurately evaluate the beauty of gemstones and to suggest new superior cuts.

One of the earliest articles on this subject, named 'Diamond Design' was published in 1919 by Tolkovski. It presents a new round cut, the values of whose parameters follow a 2D mathematical model of diamond cut and ray tracing and an optimization algorithm for brilliancy and fire.

A new horizon for finding solutions to these subjects arose with the advent of computers, when sufficient computing power became available. Then the mission of 3D gemstones modeling, 3D light modeling, 3D light ray tracing and mathematical models for gemstone's cut beauty became feasible, by using software means, hardware means or designing dedicated devices to these issues.

Stern analysis (1975) focuses on far field light pattern behavior for simulated 3D light directed perpendicular to the gem's cut table, to give suggestions of good couples of pavilion and crown angles, without broadening his ideas to suggest methods for grading gems.

Gelman (1980) simulates 3D interaction of sunlight with 3D gem cut, no restriction of simulated light direction being assumed. She suggests mathematical estimators to the gem's cut Brilliancy, Fire, Scintillation and calculates the scattering pattern of these parameters, revealed by the near field light distributions, for light that exits the stone. In addition she suggests a weighted grade based on these estimators and scattering patterns.

Shigetomi in U.S. Pat. No. 4,647,194 (March 1987) discloses a device to view the gemstone, comprising a box-like body, with a light source on its bottom, a magnifying glass equipped with a red colored disk and a viewing window on its top, and a location for the gem on its mid part. The light that emanates from the light source is reflected from the red disk, enters the stone and creates a colored light pattern view.

Yamashita in U.S. Pat. No. 5,260,763 (November 1993) discloses a device to view and photograph the gemstone, whose light source is controlled physically by a sliding semi transparent part of its tubular structure and reflected from the cylindrical interior of the tube through the gemstone to the viewing means (eye or camera).

The CGA software (CutGrade Analyzer™), after accurately scanning and measuring the diamond, evaluates and grades the diamond's light performance parameters—brilliancy, fire, and scintillation, accompanied by explanatory images and graphs. In addition it calculates and shows the scattering of this parameters, as well as the pattern of angular light directions that leave the gemstone, (viewed by near field approach, at the stone's entrance surface or leaving surface, or by far field approach). It can compare the diamond's light performance to any chosen reference stone, or to out-of-the-box reference stones corresponding to the best known cuts according to worldwide gem labs.

Gilbertston in U.S. Pat. No. 6,795,171 (September 2004) discloses a device to view the gemstone through a disk of multiple colored concentric rings, or through a cylinder of multicolored bands, to allow symmetry and brightness of the stone to be evaluated.

These devices cannot produce adequate characteristic light patterns that reveal information about the gemstone's cut symmetry: the approaches described by both Gilbertston (U.S. Pat. No. 6,785,171) and Yamashita (U.S. Pat. No. 5,260, 763) create light patterns, for restricted light entrance directions controlled by ring or band objects (U.S. Pat. No. 6,785, 171), or tubular slider position (U.S. Pat. No. 5,260,763). Since the light entry directions and the light propagation path are not homogenous, the produced patterns are not signatures that explicitly reveal the gemstone's proportions or symmetry.

The approach disclosed by Shigetomi patented that creates light patterns produced by the propagation of light reflected from a spherical disk, suffers from the same problem, and does not represent adequately the stone's proportion or symmetry.

Underwood in U.S. Pat. No. 7,193,694 (March 2007) discloses an apparatus that comprises a laser that sends a perpendicular beam to the gemstone's table, an integration sphere and a gemstone holder. While the gemstone mechanically rotates, the integration sphere measures the total intensity of light emitted by the gemstone. The data from the integration sphere are recorded, and can supply a plot of this integrated light intensity versus the rotation angle. These data are the essence of the proposed symmetry and proportion analysis. But an analysis based on these data is unable to isolate the real symmetry and proportions of the gemstone cut, but is an overall integration of symmetry properties, which misses the objective properties that are found only in specifically detailed data.

The prior art devices and methods for determination of gemstone's cut symmetry and proportion quality and quantity, fail to create a system that isolates implicitly these parameters or a process that produces data that carry exclusive information about the cut symmetry and proportion.

BRIEF SUMMARY OF THE INVENTION

The invention presents a system and method for grading and evaluating gemstones, comprising methods for evaluation and representation of a gemstone's cut symmetry and proportions quality and quantity.

The system and method according to the invention are based on creation and analysis of plurality of data sets, which convey information about the gemstone's cut symmetry and proportion quality and quantity.

These ordered data sets can contribute a significant acceleration to computerized light propagation processes for grading gemstones.

The method of organizing data sets can be done according to different predetermined laws.

In one embodiment of the system and method, a faceted gemstone is simulated, and a layer description of facets, ruled by vertical distance from the facets' center of mass to the cut sting, is added, for immediate or delayed creation of ordered data sets.

Light propagation through the 3D simulated faceted gemstone is simulated and a plurality of light propagation data sets, tagged by layer combinations along the trajectory are created and recorded.

Analysis of these ordered data sets as provided is efficient for cut grading the symmetry and proportion of gemstones.

A system according to the invention comprises:
- a processing means,
- an optical approach and model,
- a physical gemstone or a virtual 3D model of the gemstone (comprising geometry and optics of the gemstone),
- an illumination model (comprising light sources or energy sources),
- structured data recording means,
- means for modeling of the illumination propagation towards and through the gemstone and to the recording means,
- Structured recorded data,
- means for data presentation and data analysis, and
- means for evaluating cut symmetry and proportions quality and quantity.

The invention also provides a method for acceleration of grading processes based on light propagation simulation (including brilliancy, fire, scintillation etc.)

DETAILED DESCRIPTION OF THE INVENTION

1.0 Preview

The invention presents a system and method for gemstones cut grading, based on creation and analysis of plurality of data sets, conveying information about the gemstone cut symmetry and the gemstone cut proportion quality and quantity. Processes for gemstones cut grading, based on light propagation simulation, can be accelerated by using these data sets.

2.0 Environment

The environment of the invention comprises resources or processes to create or record or analyze a plurality of data sets that convey information about light patterns and trajectories of light through the gemstone's cut.

Parts of the comprised environmental resources or processes are depicted schematically in FIG. 3, FIG. 4, FIG. 5, FIG. 6, FIG. 7.

Following there is a description of another environmental component, the illumination model.

3.0 Illumination Model

The illumination model is an environmental parameter of the system according to the invention.

The illumination model can be a collection of different electromagnetic waves at the range 0.1 μm to 1 mm. It can be classified in several levels comprising:

Coherent/Non Coherent/Partial Coherent
Monochromatic/Near Monochromatic
Collection of electromagnetic waves ($0.1_{\mu m}$ to $1_{mm}$) with different wavelengths, "White" non coherent illumination (natural or man made devices),
Collimated beam,
Structured beam,
Modulated beam,
Laser beam TEM00 or TEM factor sq M,
Wave pocket, In a preferred embodiment the illumination is sunlight or monochromatic.

Other embodiments, for different illumination models, can be employed without departing from the spirit and scope of the present invention, as would be apparent for one skilled in the relevant art.

In order to simplify the description of the invention, next we focus on a description of preferred embodiments.

Other embodiments can be employed without departing from the spirit and scope of the present invention, as would be apparent for one skilled in the relevant art.

4.0 Description of One Preferred Embodiment of the Invention

Figure 14:
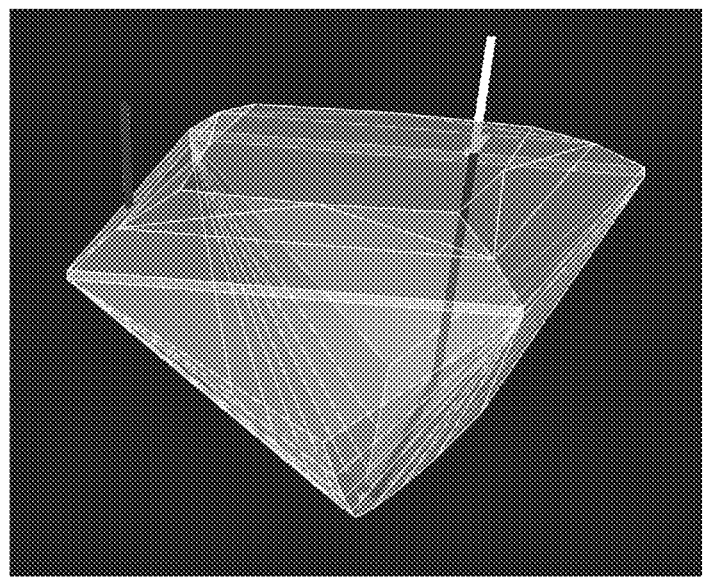
FIG. 14 shows a ray light propagation through a gemstone model, for a princess diamond cut.

In accordance with one preferred embodiment, the invention application is performed by a computerized simulation. Output light distribution patterns tagged by facets' group combinations are calculated, for simulated light that propagates through the gemstone's cut, where the gemstone is a 3D faceted geometric object (see examples in FIG. 9 and FIG. 14) and the illumination is sunlight or monochromatic and is directed toward the stone perpendicular to the cut's table plane, and simulated in reverse.

Figure 10A:
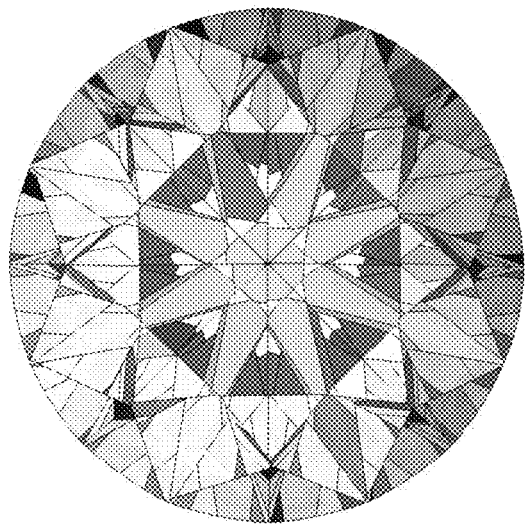
FIGS. 10($a$) and 10($b$) show light distribution patterns of a brilliant cut for output light near field approach model 204. The cut in FIG. 10($b$) is rotated upside down by 180 degrees relative to the cut in FIG. 10($a$).
Figure 10B:
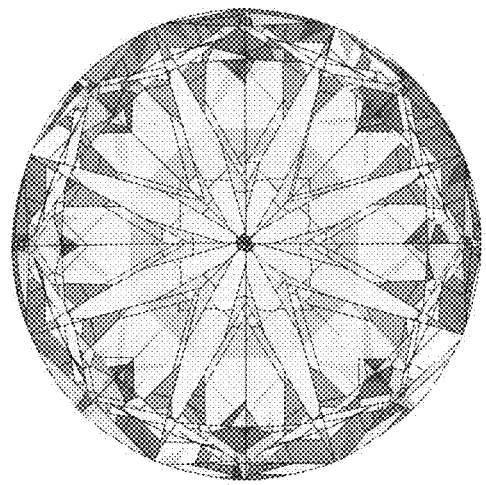
Figure 15A:
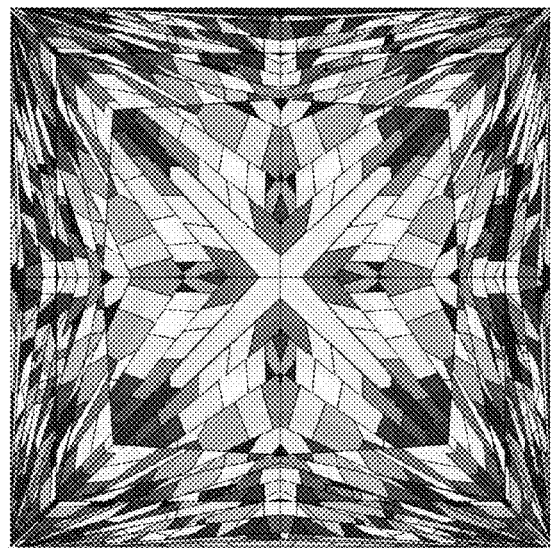
FIGS. 15($a$) and 15($b$) show light distribution patterns of a princess cut for an output light near field approach model 204. The cut of FIG. 15($b$) is rotated upside down by 180 degrees relative to the cut of FIG. 15($a$).
Figure 15B:
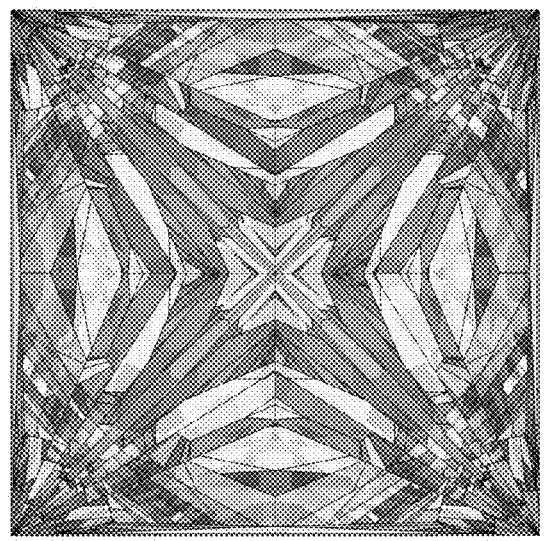

See examples of output light distribution patterns for a near field approach model 204:
for a brilliant cut, in FIG. 10(*a*),
for rotated (upside down) brilliant cut in FIG. 10(*b*),
for a princess cut in FIG. 15(*a*),
for rotated (upside down) princess cut in FIG. 15(*b*).

Figure 11:
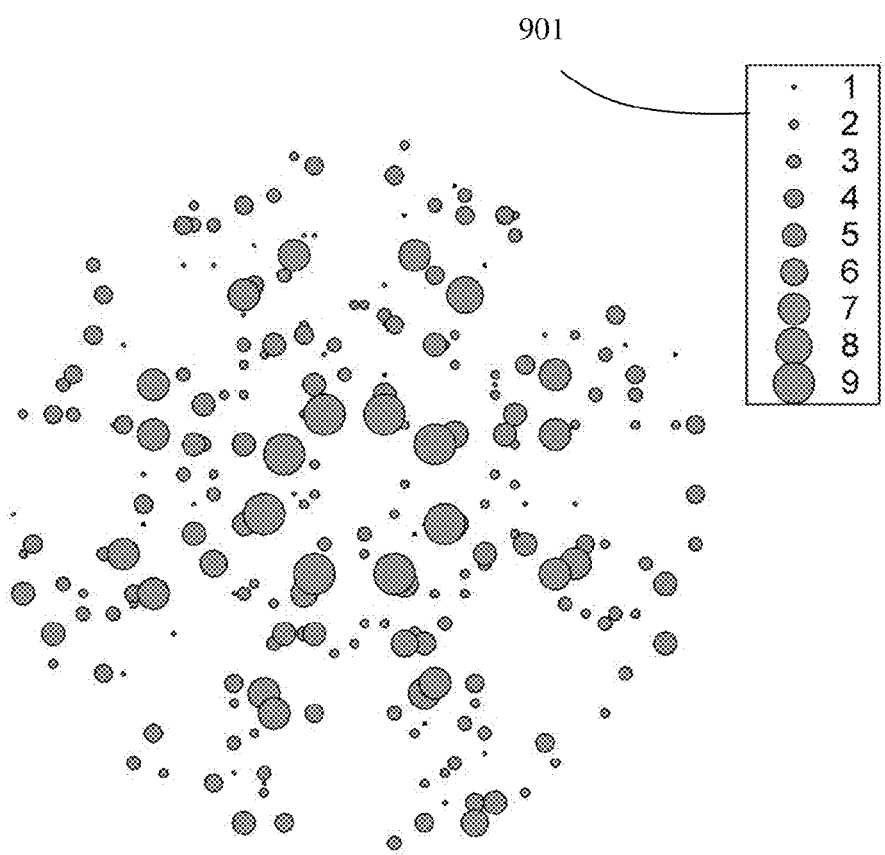
FIG. 11 shows the light distribution pattern accepted by far field approach model 203, and recorded on the output surface 207, for a brilliant cut.
Figure 16:
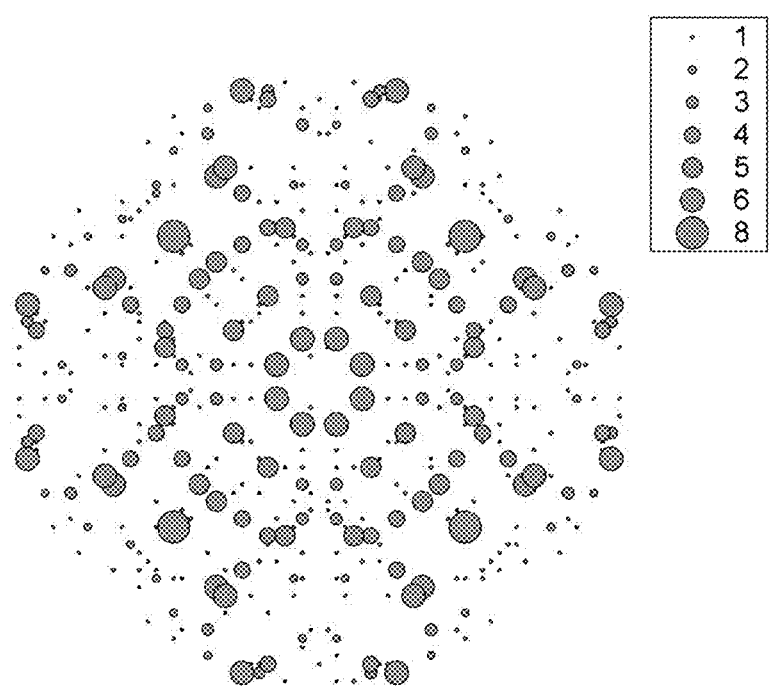
FIG. 16 shows the light distribution pattern accepted by a far field approach model 203, and recorded on an output surface 207, for a princess cut.

See examples of output light distribution patterns for a far field approach model 207:
for a brilliant cut in FIG. 11,
for a princess cut in FIG. 16.

The comprised groups of facets are for groups determined by layers description of facets, ruled by vertical distance from the facets center of mass to the cut sting. See three examples of facets groups: one example for brilliant cut in FIG. 12 and two examples for princess cut, in FIG. 18 and in FIG. 20.

Figure 1:
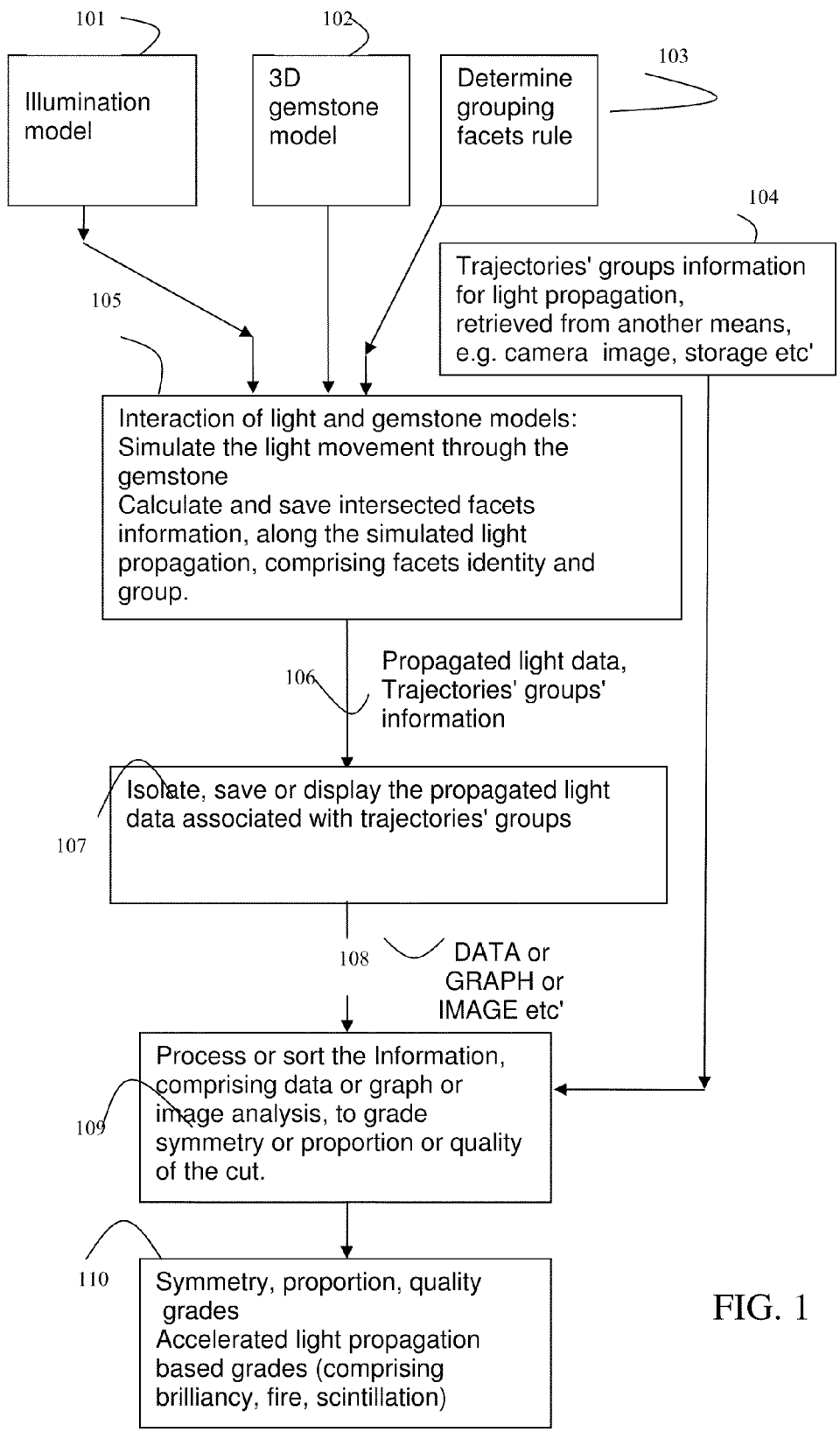
FIG. 1 is a flow chart of procedures for evaluation of cut symmetry and proportions quality and quantity.
Figure 2:
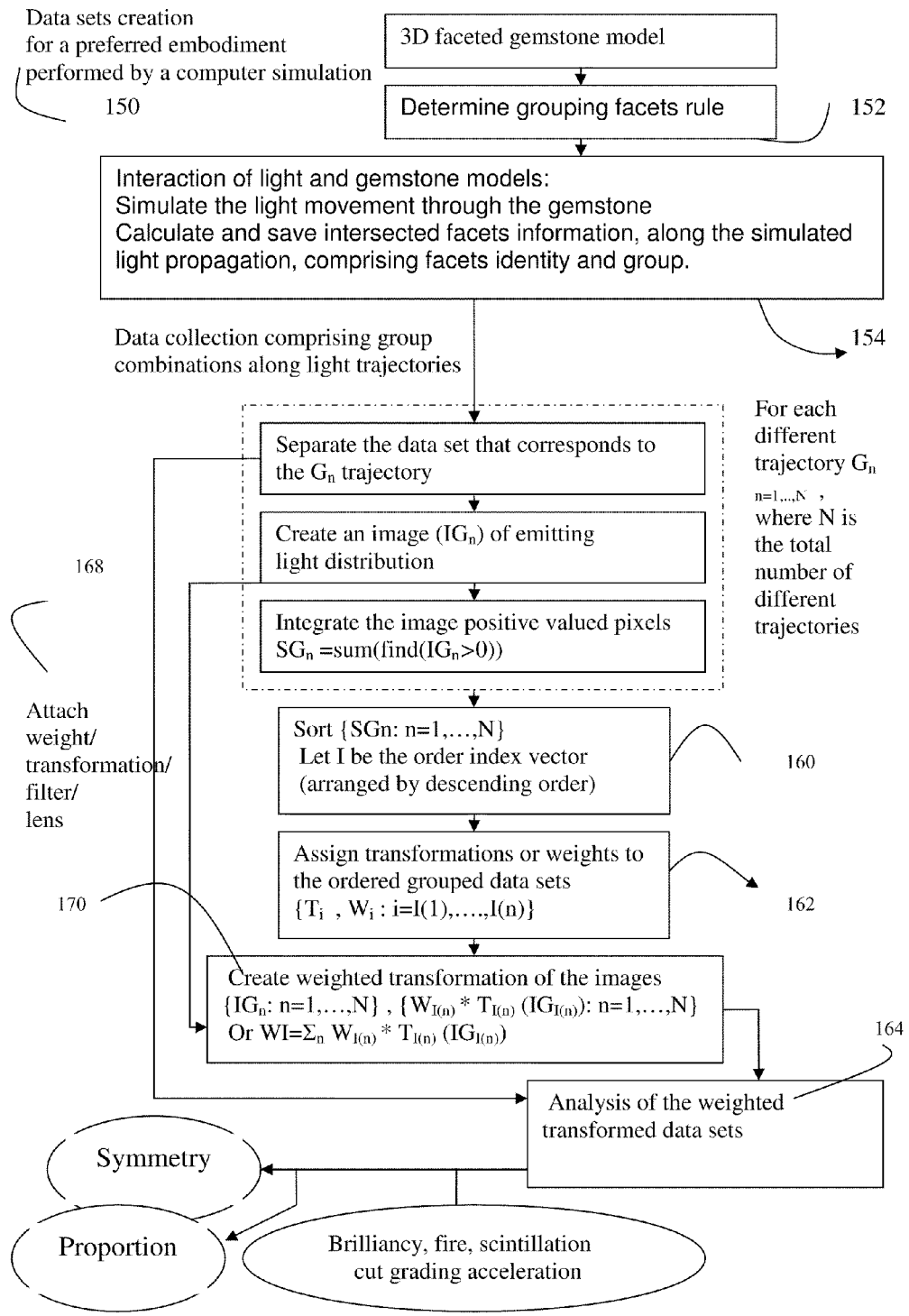
FIG. 2 is a flow chart of data sets creation for a preferred embodiment performed by a computer simulation.
Figure 7:
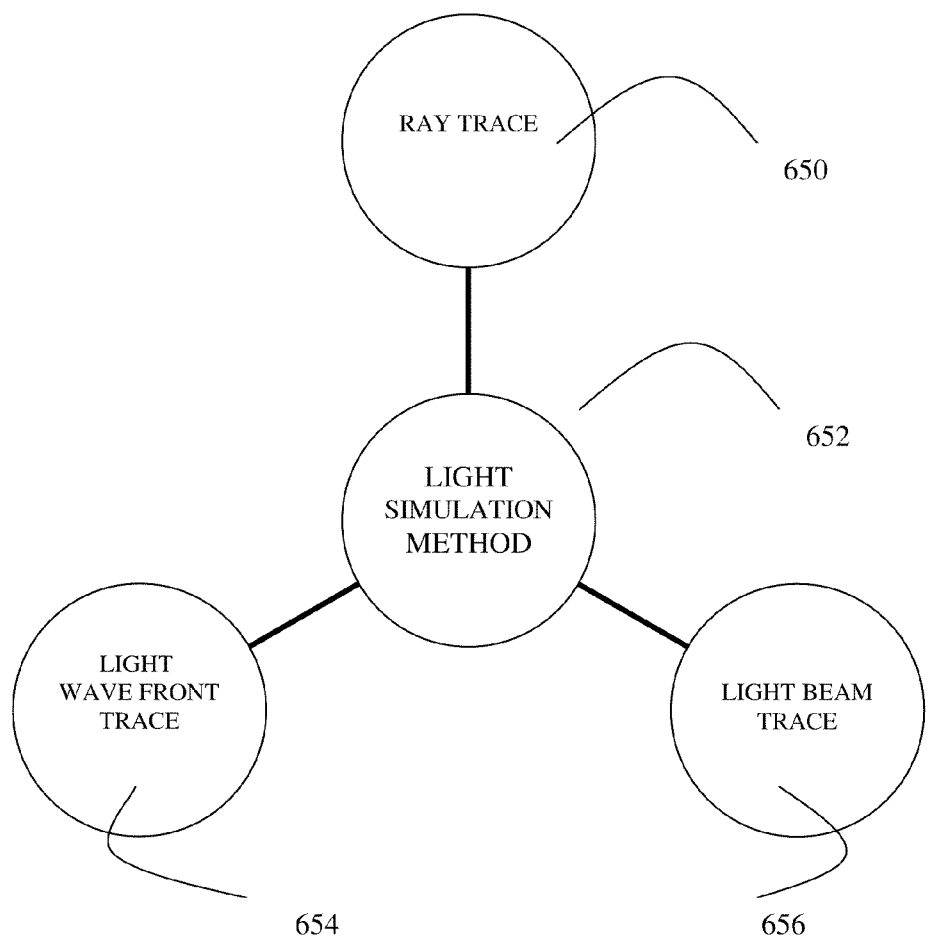
FIG. 7 is a diagram of optional methods of light trace simulation, for an embodiment of the invention realized by light propagation simulation.
Figure 8:
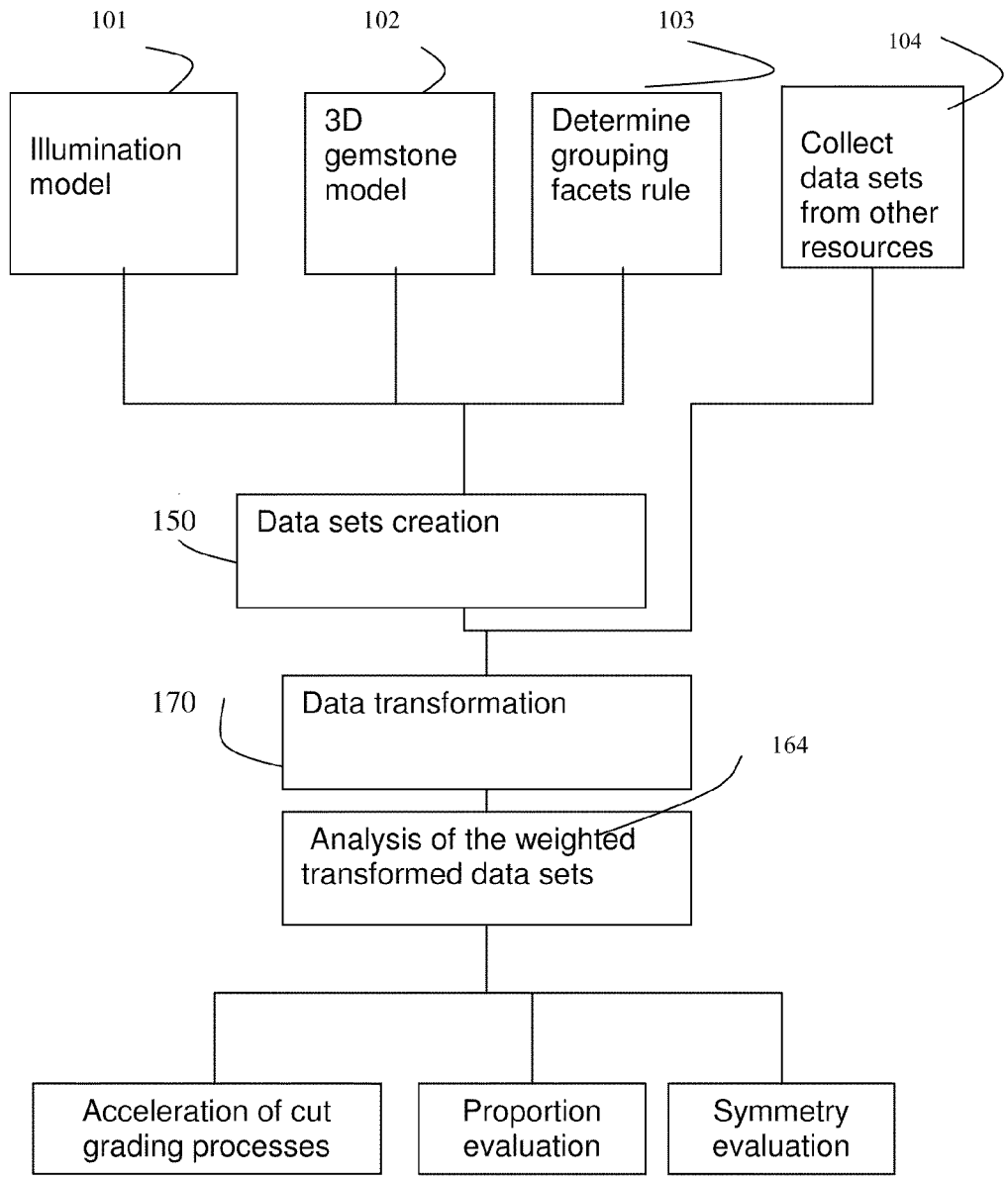
FIG. 8 shows a flow chart illustrating the main steps for evaluation of gemstones.

In a preferred embodiment of the invention, the simulation of light propagation follows ray trace method 650 or wave front trace method 654, as shown in FIG. 7. The traced light propagation is recorded and creates a data base 154, together with added facet's group values, and groups' trajectory. This data base can be used for immediate or later creation of a plurality of light propagation data sets, or of a plurality of light distribution data sets, tagged by groups' path combinations. FIG. 2 shows a flow chart of the method of creation and processing data sets for a preferred embodiment based on computer simulation.

Referring to the flow chart on FIG. 2, the light distribution pattern images comprised in the data sets are either sorted in step 160, where in one preferred embodiment the sorting parameter is the illuminated area integral or the light intensity image integral, or mapped, see steps 168, 170, in another illustrative preferred embodiment.

In one preferred embodiment the weights $w_i$ in step 160 get value w=1 for i<=K, and $w_i$=0

Figure 3:
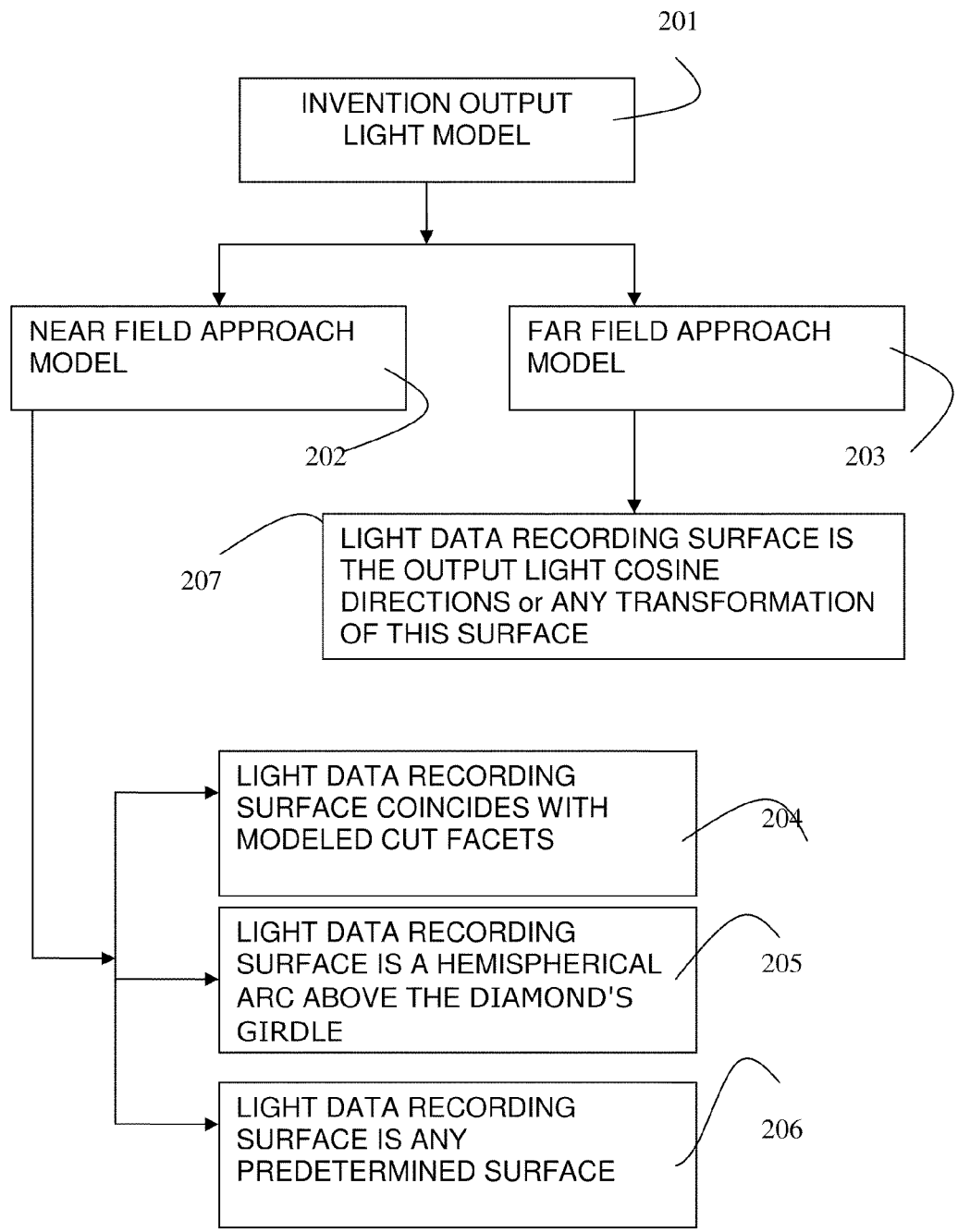
FIG. 3 is a diagram of optional output light models.
Figure 4:
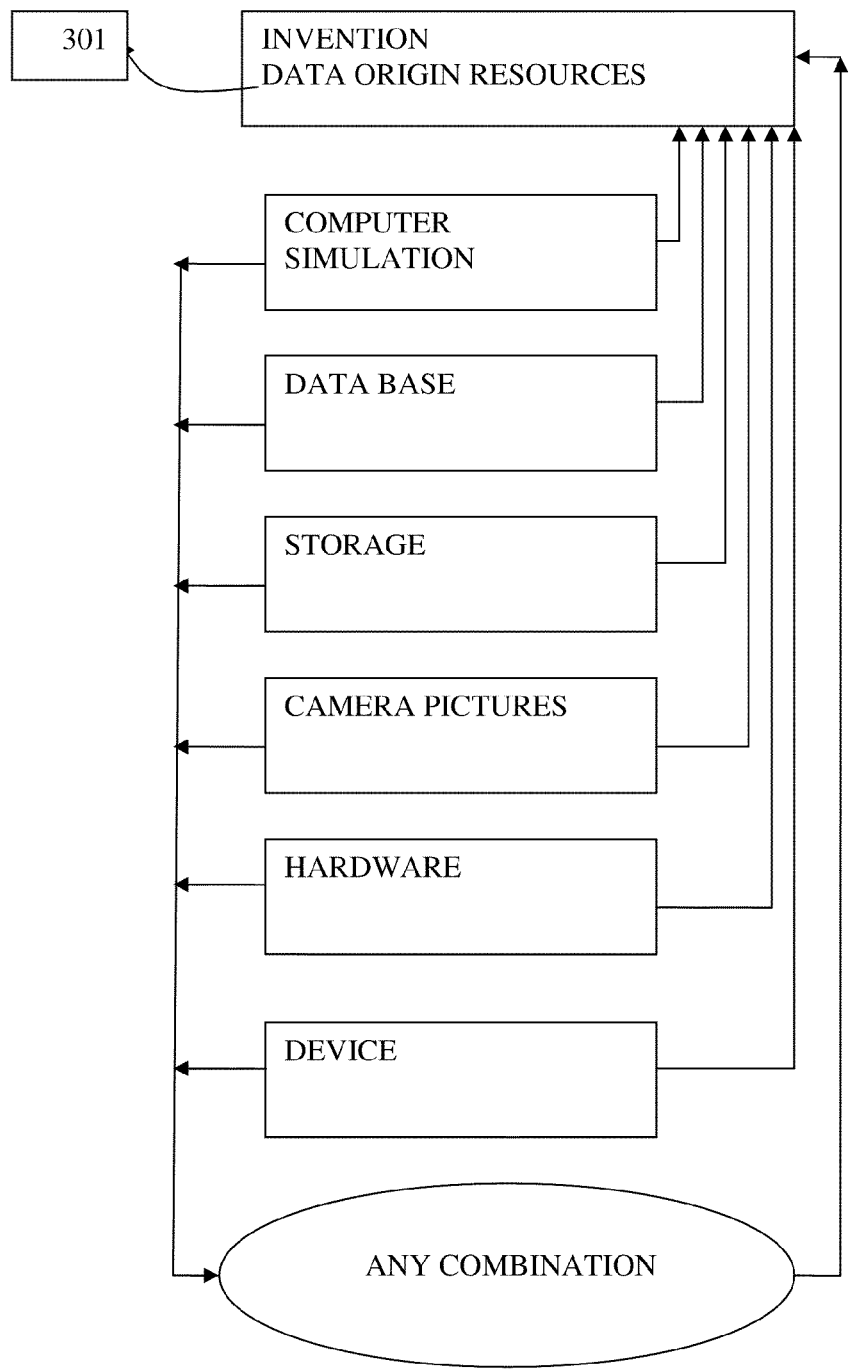
FIG. 4 is a diagram of optional data origin resources.
Figure 5:
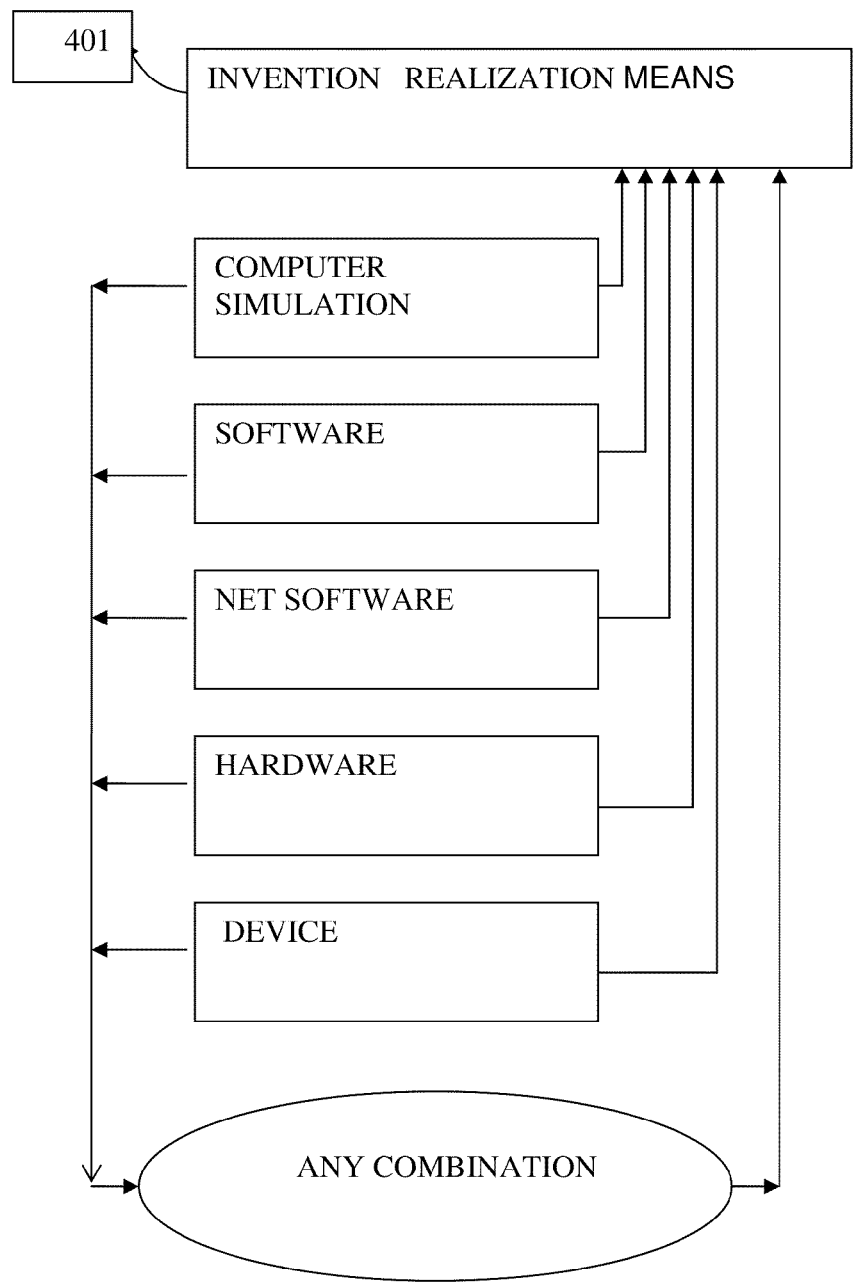
FIG. 5 is a diagram of optional invention realization means.
Figure 6:
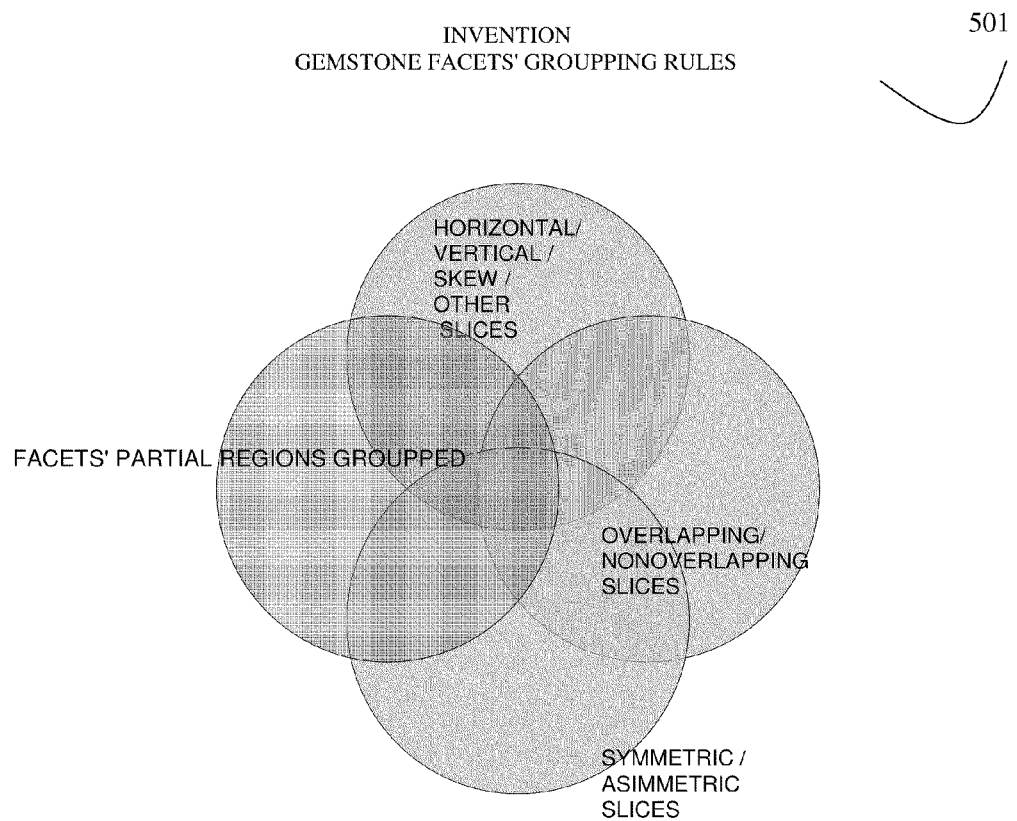
FIG. 6 is a diagram of optional logic for making rules that control the grouping process of the gemstone's facets or sub regions of facets.

For i>K, where 1<=K<=N (N: total number of trajectories groups), and K is chosen to fulfill the requirement that the mask generated by the sum of images $\{IG_{I(n)}:1<=n<=K\}$ covers a required percentage (e.g. 90%) of the intensity mask of the output light surface 202 in FIG. 3.

Figure 9:
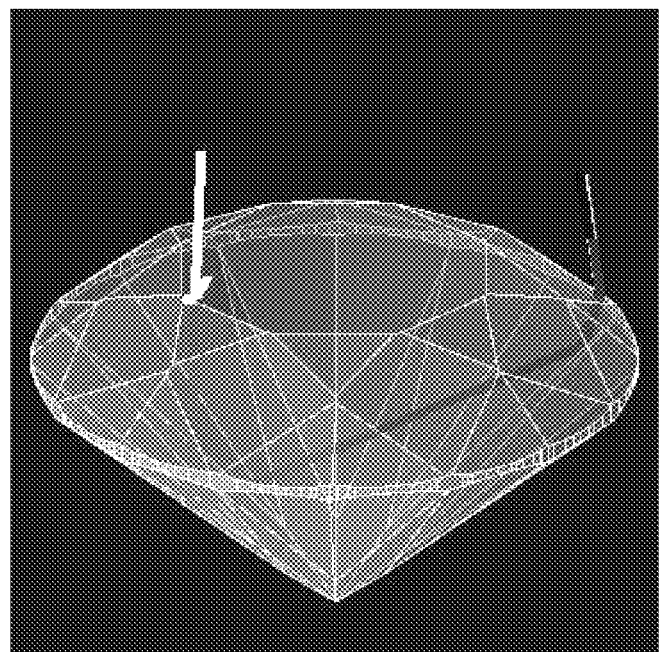
FIG. 9 shows a ray light propagation through a gemstone model, for a brilliant diamond cut.
Figure 12:
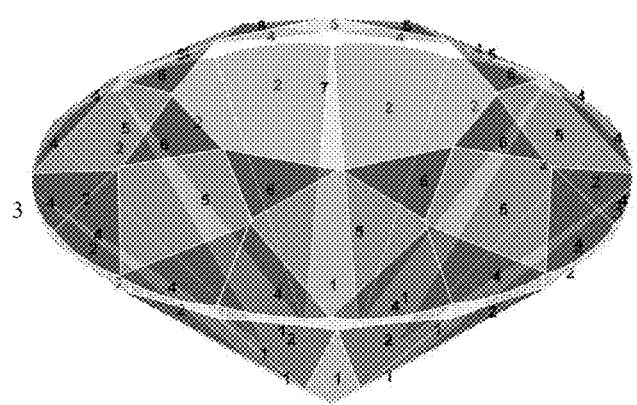
FIG. 12 shows a brilliant gemstone cut model whose facets are partitioned to groups, defined by the range of the $3^{rd}$ axes of the facets central gravity point, to the $3^{rd}$ axes zero point. Alternating black and white colors mark the different facets groups.
Figure 13A:
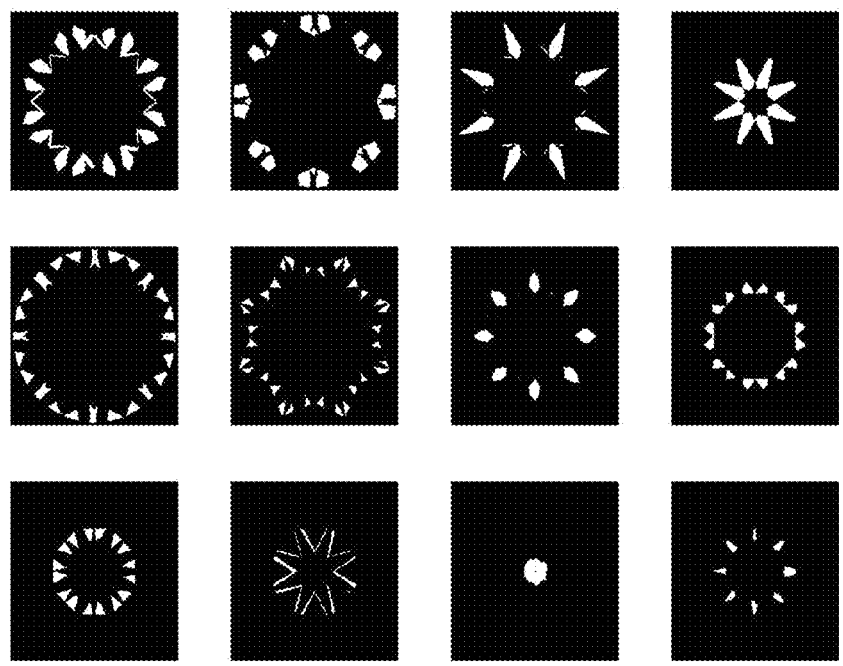
FIGS. 13($a$) through 13($d$) show the light data patterns associated with group trajectories, for one embodiment of scenario of light and gemstone, and of group trajectories selection and representation (collected while simulating light propagation through the gemstone of FIG. 7).
Figure 13B:
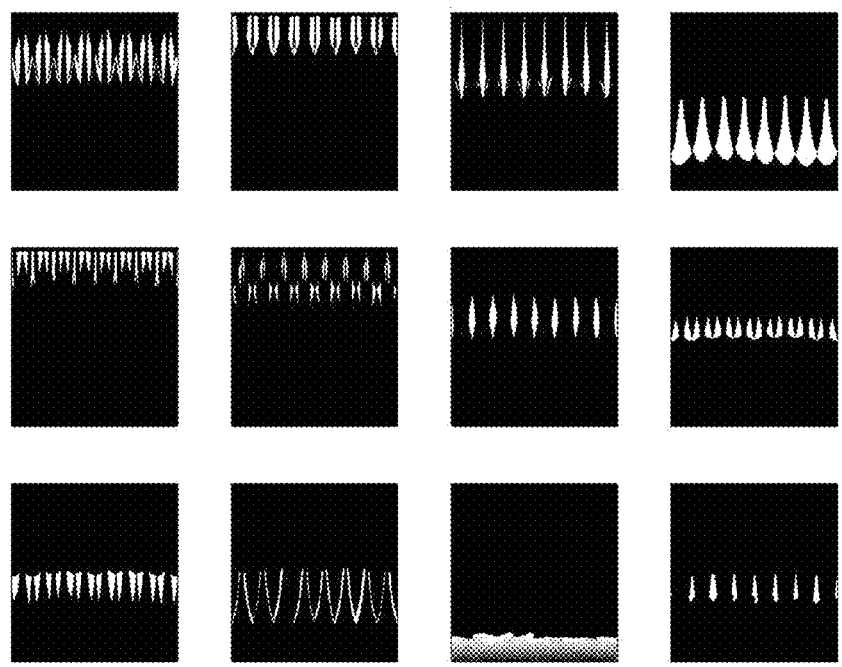
Figure 13C:
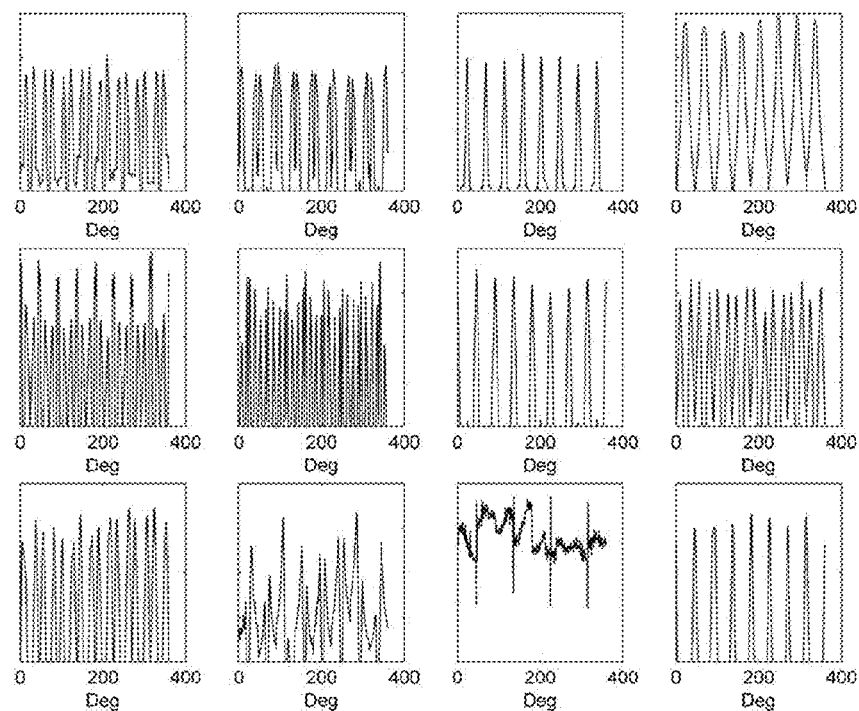
Figure 13D:
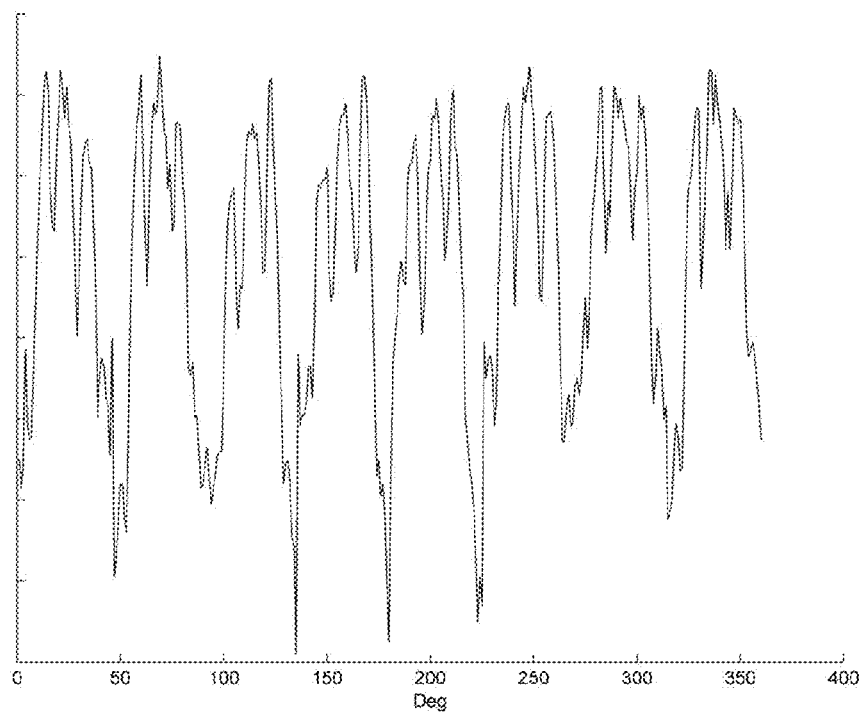
Figure 18:
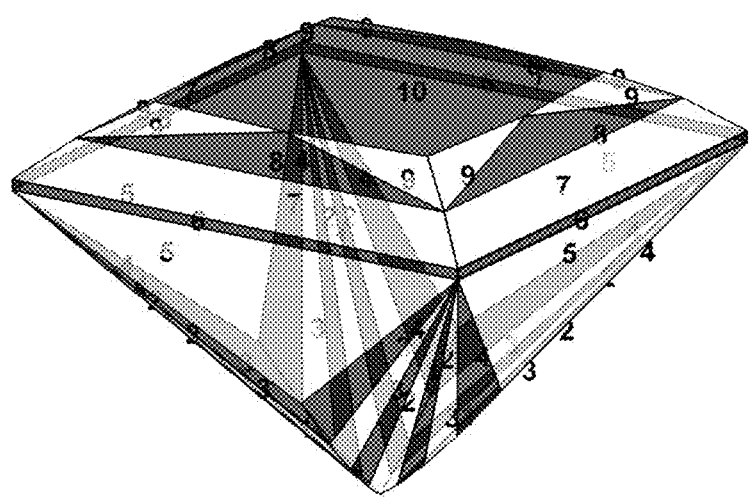
FIG. 18 shows a princess gemstone cut model whose facets are partitioned to groups, defined by the range of the $3^{rd}$ axes of the facets central gravity point, to the $3^{rd}$ axes zero point. Alternating black and white colors mark the different facets groups.
Figure 19A:
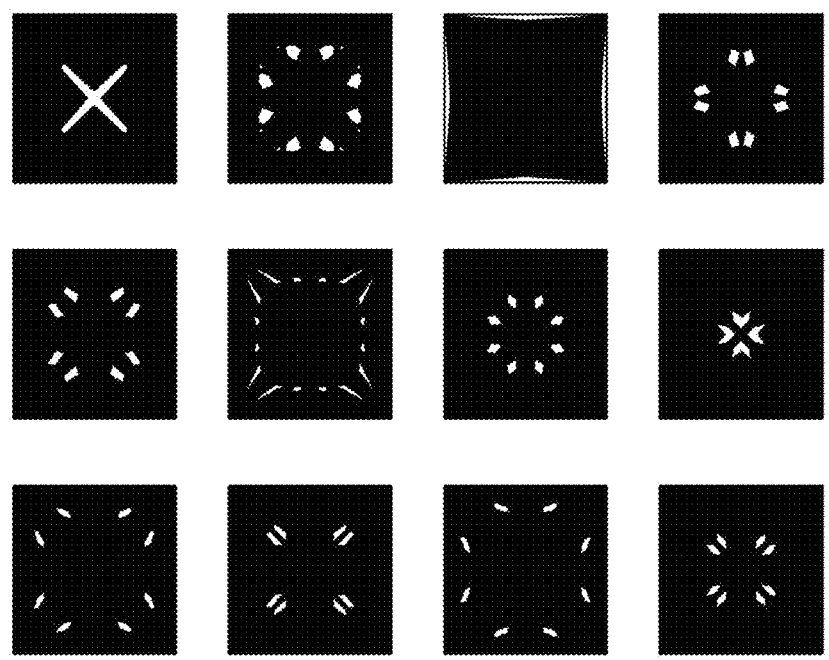
FIGS. 19($a$) through 19($d$) show the light data patterns associated with group trajectories, for one embodiment of scenario of light and gemstone, and of group trajectories selection and representation (collected while simulating light propagation through the gemstone of FIG. 14, for several light trajectories retrieved using the facets grouping rule of FIG. 18).
Figure 19B:
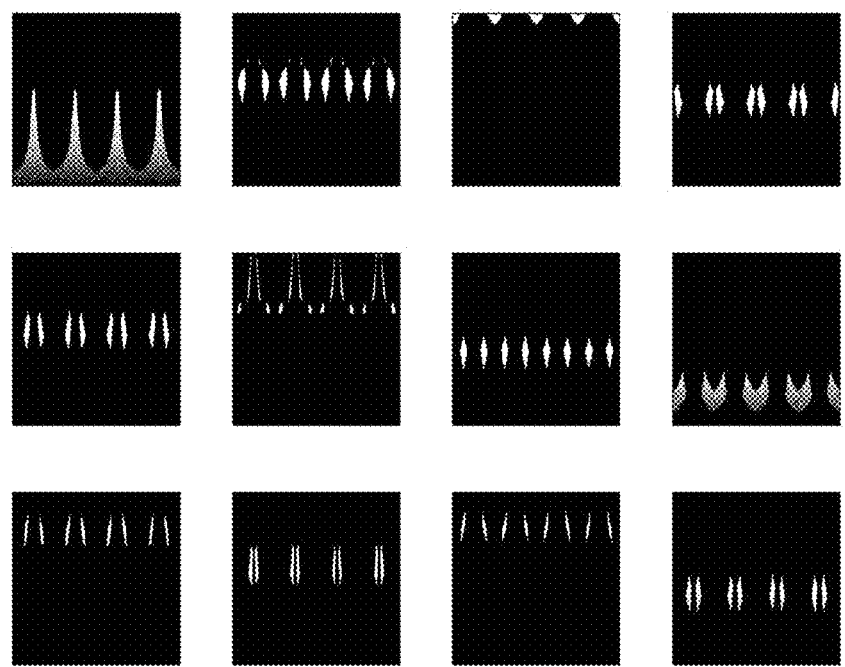
Figure 19C:
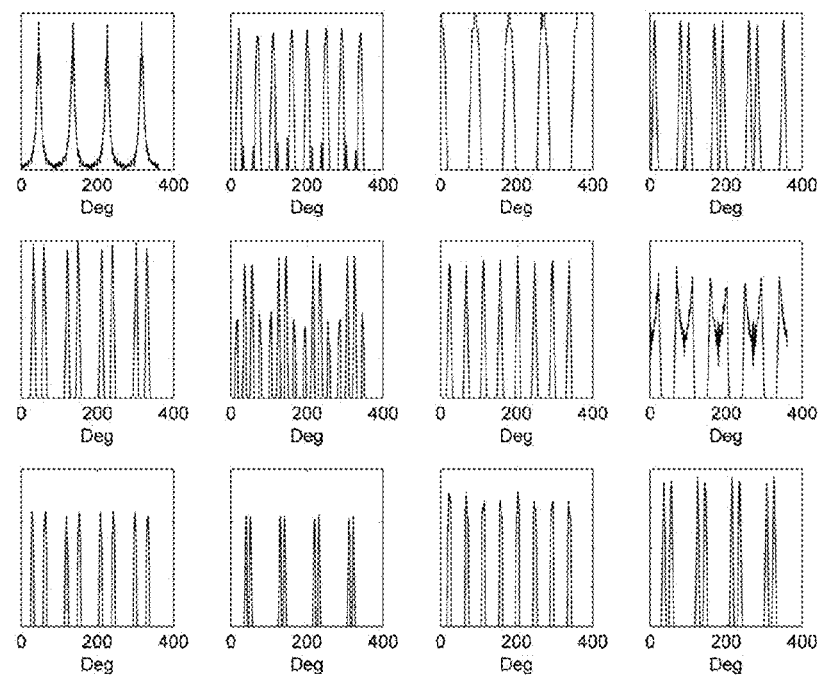
Figure 19D:
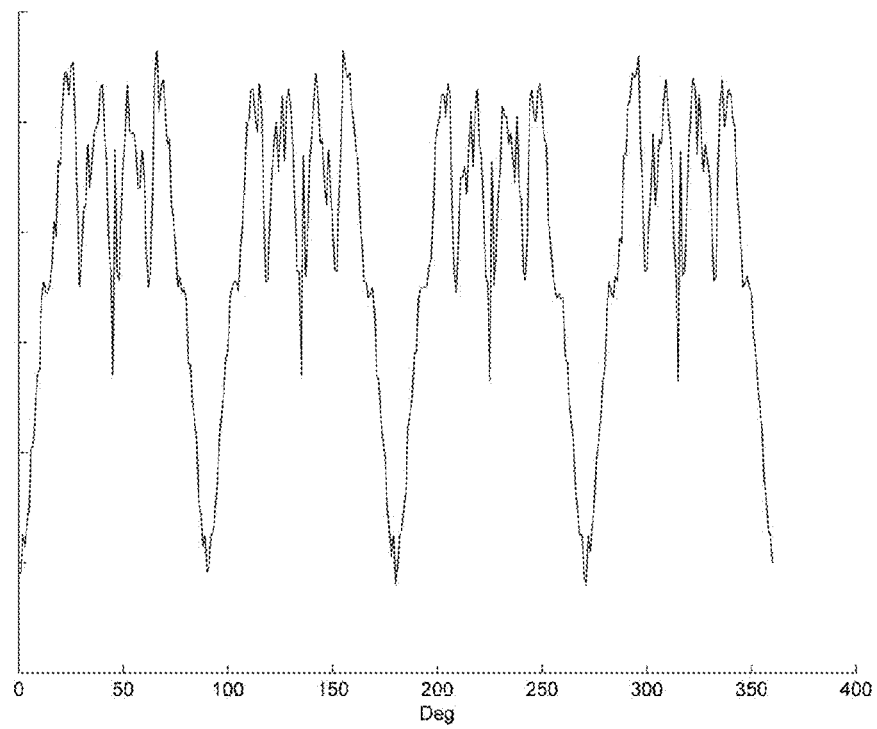
Figure 20:
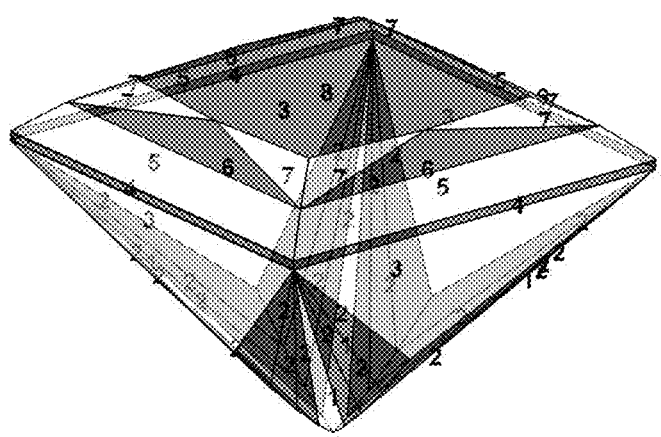
FIG. 20 is princess gemstone cut model whose facets are partitioned to groups, defined by range intervals of the $3^{rd}$ axes of the facets central gravity point, to the $3^{rd}$ axes zero point. Alternating black and white colors mark the different facets groups.
Figure 21A:
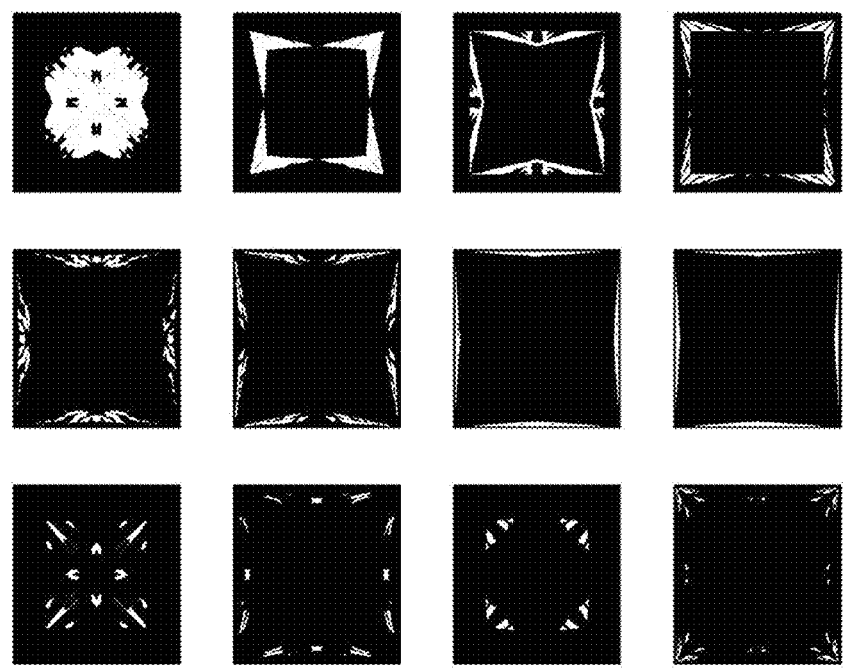
FIGS. 21($a$) through 21($d$) show the light data patterns associated with group trajectories, for one embodiment of scenario of light and gemstone, and of group trajectories selection and representation (collected while simulating light propagation through the gemstone of FIG. 14, for several light trajectories retrieved using the facets grouping rule of FIG. 20).
Figure 21B:
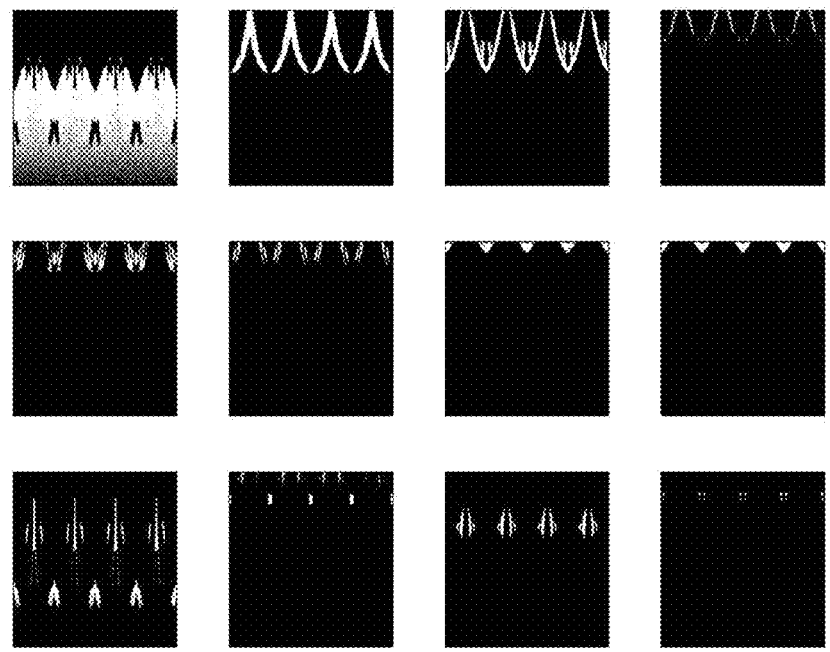
Figure 21C:
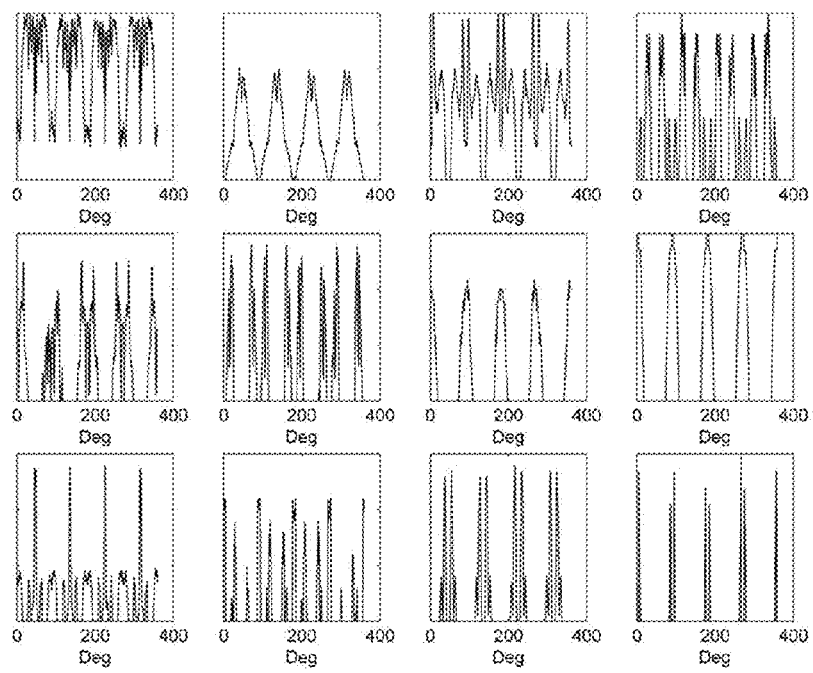
Figure 21D:
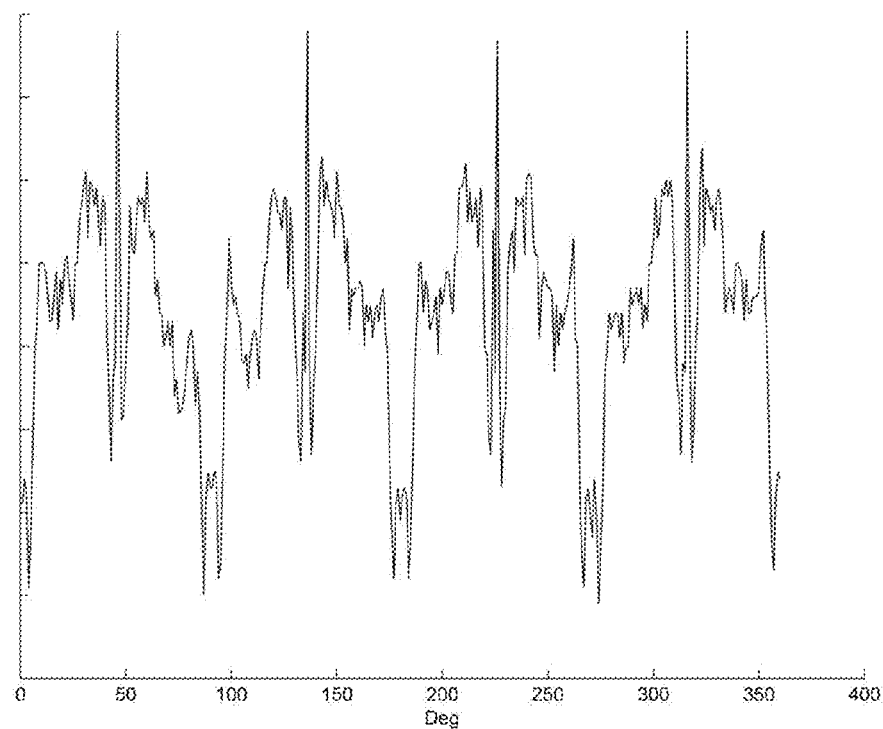
Figure 22A:
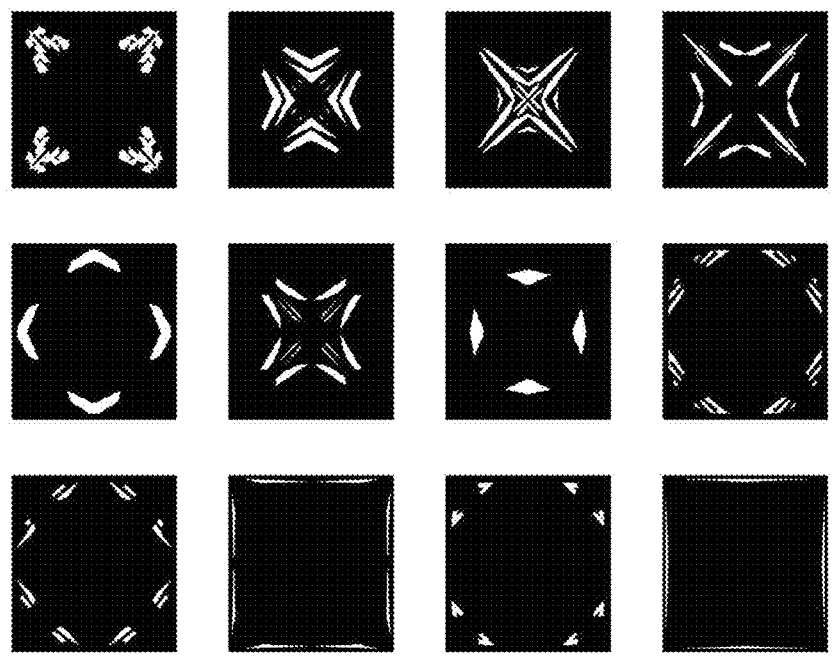
FIGS. 22($a$) through 22($d$) show the light data patterns associated with group trajectories, for one embodiment of scenario of light and gemstone, positioned upside down, and of group trajectories selection and representation (collected while simulating light propagation through the gemstone of FIG. 14, rotated by 180 degrees upside down and for several light trajectories retrieved using the facets grouping rule of FIG. 20).
Figure 22B:
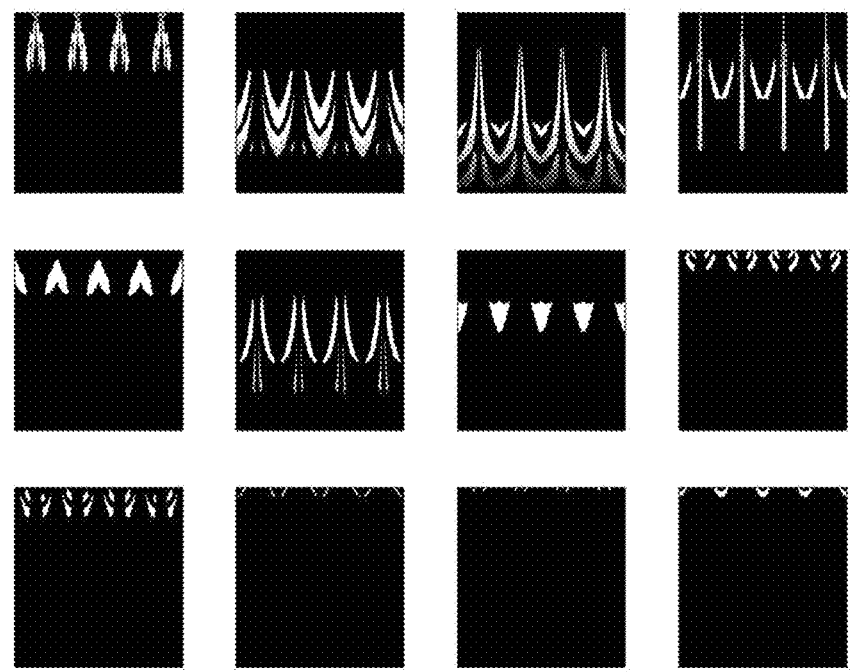
Figure 22C:
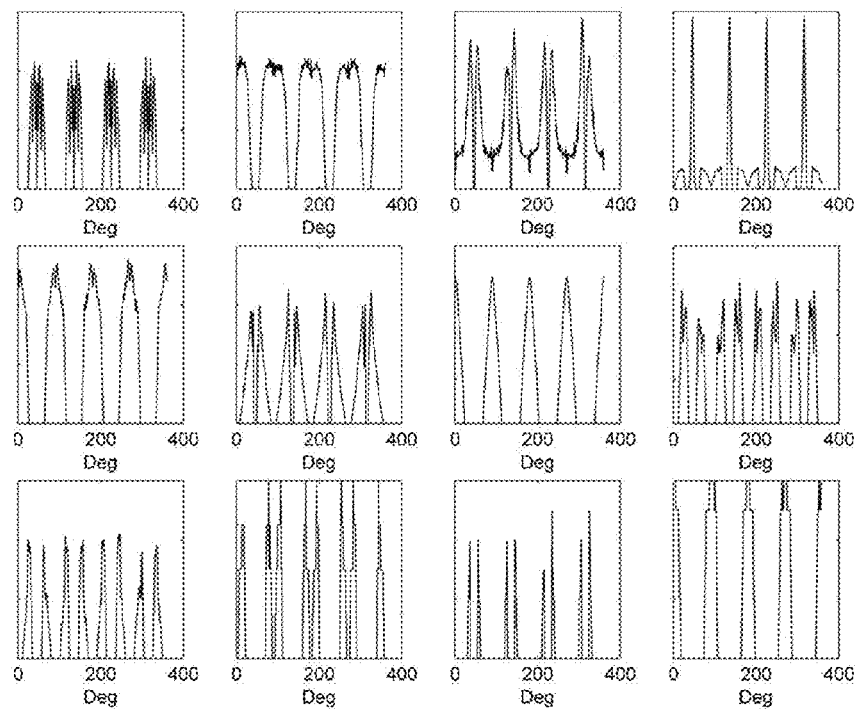
Figure 22D:
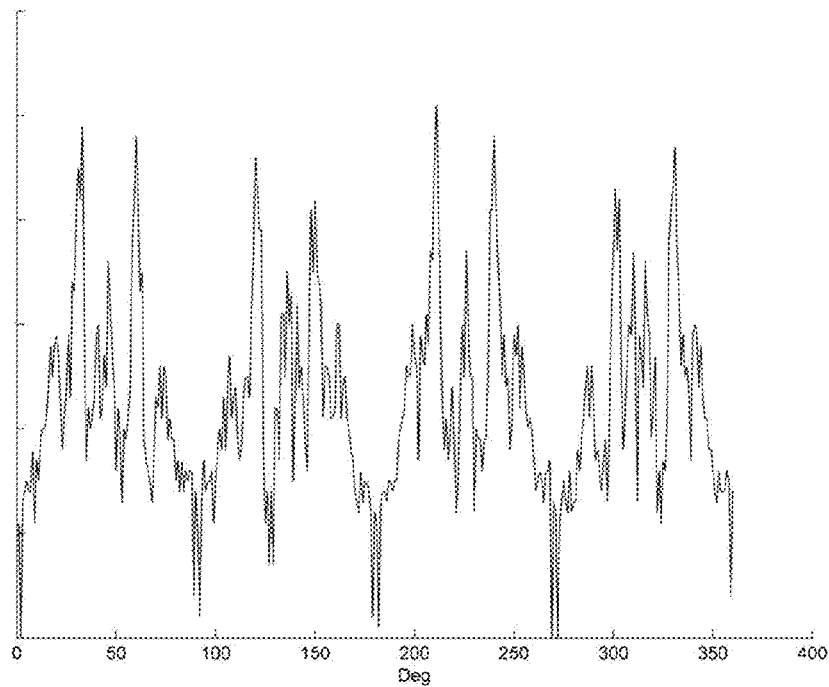

Referring to the light propagation data sets, FIG. 13(*a*) exemplifies images, for the brilliant cut of FIG. 9 and facets groups as shown in FIG. 12. Thus, FIG. 13(*a*) shows the images:
$\{IG_{I(n)}>0:1<=n<=12\}$. Each image refers to a unique path of facets' groups, and is a black/white colored image that shows the mask of a light pattern for an output light model surface 202. Referring to the number of data sets presented at FIG. 13, they are positioned at the 1, . . . , 12 indexes on the sorted data sets list, 160 in FIG. 2. Similarly, FIG. 19(*a*) exemplifies this embodiment's data base, for the princess cut of FIG. 14 and facets groups as shown in FIG. 18. FIG. 21(*a*) exemplifies images, for the princess cut of FIG. 14 and facets groups as shown in FIG. 20. FIG. 22(*a*) exemplifies images, for the rotated upside down, princess cut of FIG. 14 and facets groups as shown in FIG. 20.

FIGS. 13(*b*), 19(*b*), 21(*b*), 22(*b*) present transformed images of the images in FIGS. 13(*a*), 19(*a*), 21(*a*), 21(*a*) respectively, where the transformation is from Cartesian coordinates to polar coordinates (range versus 0-360 degrees).

FIGS. 13(*c*), 19(*c*), 21(*c*), 22(*c*) present graph images originated from the images in FIGS. 13(*b*), 19(*b*), 21(*b*) respectively, where the $n^{th}$ graph (1<=n<=12) integrates the $n^{th}$ image in the range direction, to show the sum (covered area) versus degree (0-360 deg.)

FIGS. 13(*d*), 19(*d*), 21(*d*), 22(*d*) are graphs of weighted sums of the image graphs presented in FIGS. 13(*c*), 19(*c*), 21(*c*), 22(*c*) respectively.

The symmetry of these graphs reflects the gemstone's symmetry. It can be calculated by methods like dividing a graph into sub graphs, and measuring the mutual correlation between these sub graphs. The number of sub graphs corresponds to the predicted symmetry we try to find or evaluate.

The proportion quality of the gemstone can be revealed by detection of the extreme values on these sub graphs that correspond to the relevant symmetry. These values are compared to yield a measure of the gemstone's proportion.

Figure 17:
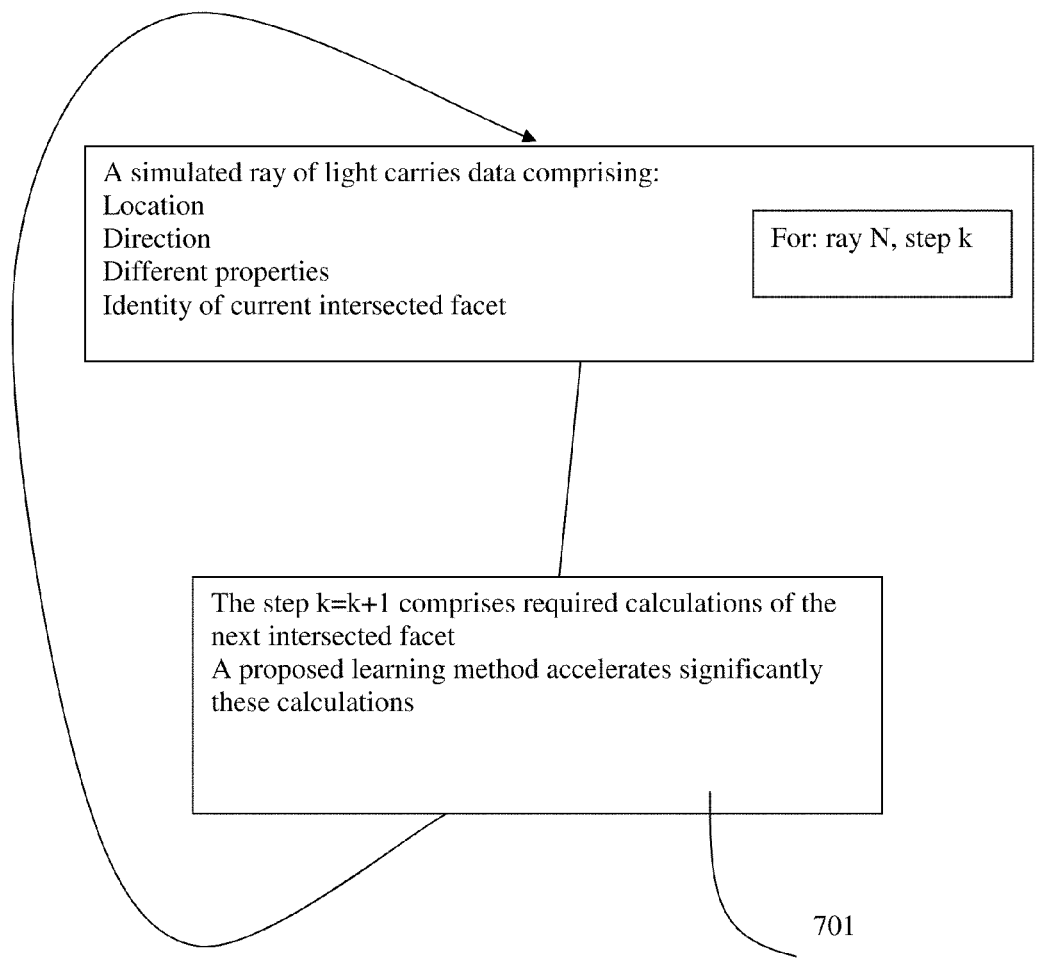
FIG. 17 shows a flow chart of one step from a traveling ray intersection with the gemstone.

Methods for cut grading gemstones based on a simulation of the light interaction with a gemstone can be accelerated by the disclosed application. For any specific gemstone, e.g. 57 faceted round cut, once we calculate the group combinations as described in our invention, the simulation procedure step presented on FIG. 17, to determine the next facet 701 is accelerated. This acceleration is achieved by reducing the sample space of possible facets needed to be checked for fulfilling certain requirements. Namely, we propose here a learning method of the next facet step 701 on FIG. 17 for ray intersection with a gemstone.

The following models and processes can be employed by getting a variety of values without departing from the spirit and scope of the present invention, as would be apparent for one skilled in the relevant art:
the output light model 201,
the data origin resources 301,
the realization means 401,
the grouping rules logic base 501,
the grouping rules 103, 152,
the weights and mapping 162,
the light simulation method 652, in an embodiment that comprises light simulation,
the value and order of applied weights and mapping 162, and of sorting process 160, applied to data sets, and
the analysis algorithm of the data sets.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

What is claimed is:

1. A computer-implemented method for grading symmetry or proportion of a multifaceted gemstone using a mathematical model of the gemstone stored in a computer-readable memory, said method comprising:
    determining groups of facets of said gemstone wherein each group of facets contains a respective subset of facets that are related to each other according to a predetermined axis of symmetry;
    simulating transmission of a plurality of simulated electromagnetic waves through the gemstone so as to propagate via successive facets according to their related geometry and optical characteristics;
    associating the simulated electromagnetic waves with a respective trajectory group such that all of the simulated electromagnetic waves in each trajectory group strike facets in identical groups of facets and in an identical sequence;
    for each trajectory group, determining a respective dataset representative of the energy collected on a predetermined surface or a function thereof; and
    using said datasets to determine a measure of symmetry or proportion of the gemstone along said axis.

2. The method according to claim 1, wherein simulating transmission of a plurality of simulated electromagnetic waves through the gemstone includes determining successive facets through which a simulated electromagnetic wave propagates by:
    iteratively determining whether there exists a preferred matching trajectory group in said trajectory groups sorted in order of preference according to whether successive facets through which the simulated electromagnetic wave has so far propagated correspond to said preferred trajectory group;
    while a preferred matching trajectory exists, making an attempt to trace the simulated electromagnetic wave through successive facets in the preferred matching trajectory group; and
    only if no preferred matching trajectory exists or said attempt fails, tracing the simulated electromagnetic wave through all facets in the mathematical model.

3. The method according to claim 2, including:
    compiling a subset of trajectory groups for a gemstone of a given cut gemstone shape wherein a probability that simulated electromagnetic waves will pass through a trajectory in said subset exceeds a given threshold;
    whereby simulating transmission of simulated electromagnetic waves through another gemstone of identical cut gemstone shape is accelerated by first making an attempt to simulate transmission via a trajectory group in said subset, and
    only if said attempt fails, simulating transmission through all facets.

4. The method of claim 1, wherein the dataset is representative of energy locations on the predetermined surface where the energy is distributed.

5. The method of claim 1, wherein a measure of symmetry of the energy on said surface in each dataset represents a corresponding measure of symmetry of the gemstone and using said datasets to determine a measure of symmetry or proportion of the gemstone along said axis comprises:
    (a) ordering a subset of the datasets in descending order of cumulative energy;
    (b) spatially separating the energy locations on said surface into distinct groups of linearly separated clusters;
    (c) computing a cumulative energy or a function thereof in each cluster and a linear separation between clusters;
    (d) repeating (b) and (c) for all datasets in the subset; and
    (e) computing a measure of symmetry or proportion of the gemstone relative to said axis of symmetry from the cumulative energies or functions thereof and linear separations between clusters.

6. The method of claim 5, including determining a proportion quality of the gemstone by detecting extreme values of said cumulative energies or functions thereof and using said values to yield a measure of the gemstone's proportion.

7. The method of claim 5, wherein spatially separating comprises filtering or weighted transformation of said datasets.

8. The method of claim 1, wherein said simulated electromagnetic waves comprise light emitted from simulated illumination sources.

9. The method of claim 1, wherein said predetermined surface, comprises any one of the following:
    the gemstone surface,
    a spherical surface centered at a girdle center of the gemstone,
    a spherical surface centered at a table center of the gemstone,
    a far field surface for the simulated electromagnetic waves.

10. A non-transitory computer readable memory storing program instructions, which when run on a computer, cause the computer to execute a method for grading symmetry or proportion of a multifaceted gemstone using a mathematical model of the gemstone stored in a computer-readable memory, said method comprising:
    determining groups of facets of said gemstone wherein each group of facets contains a respective subset of facets that are related to each other according to a predetermined axis of symmetry;
    simulating transmission of a plurality of simulated electromagnetic waves through the gemstone so as to propagate via successive facets according to their related geometry and optical characteristics;
    associating each of the simulated electromagnetic waves with a respective trajectory group such that all of the simulated electromagnetic waves in each trajectory group strike facets in identical groups of facets and in an identical sequence;
    for each trajectory group, determining a respective energy collected on a predetermined surface or a function thereof; and
    using said respective energy or functions thereof to determine a measure of symmetry of the gemstone along said axis.

11. The non-transitory computer readable memory of claim 10, wherein simulating transmission of a plurality of simulated electromagnetic waves through the gemstone includes determining successive facets through which a simulated electromagnetic wave propagates by:
    iteratively determining whether there exists a preferred matching trajectory group in said trajectory groups sorted in order of preference according to whether successive facets through which the simulated electromagnetic wave has so far propagated correspond to said preferred trajectory group;

while a preferred matching trajectory exists, making an attempt to trace the simulated electromagnetic wave through successive facets in the preferred matching trajectory group; and only if no preferred matching trajectory exists or said attempt fails, tracing the simulated electromagnetic wave through all facets in the mathematical model.

12. The non-transitory computer readable memory according to claim 11, where said method includes:

compiling a subset of trajectory groups for a gemstone of a given cut gemstone shape wherein a probability that simulated electromagnetic waves will pass through a trajectory in said subset exceeds a given threshold;

whereby simulating transmission of simulated electromagnetic waves through another gemstone of identical cut gemstone shape is accelerated by first making an attempt to simulate transmission via a trajectory group in said subset, and only if said attempt fails, simulating transmission through all facets.

13. The non-transitory computer readable memory of claim 10, wherein a measure of symmetry of the energy on said surface in each dataset represents a corresponding measure of symmetry of the gemstone and using said datasets to determine a measure of symmetry or proportion of the gemstone along said axis comprises:

(a) ordering a subset of the datasets in descending order of cumulative energy;
(b) spatially separating the energy locations on said surface into distinct groups of linearly separated clusters;
(c) computing a cumulative energy or a function thereof in each cluster and a linear separation between clusters;
(d) repeating (b) and (c) for all datasets in the subset; and
(e) computing a measure of symmetry or proportion of the gemstone relative to said axis of symmetry from the cumulative energies or functions thereof and linear separations between clusters.

14. The non-transitory computer readable memory of claim 13, wherein the method includes determining a proportion quality of the gemstone by detecting extreme values of said cumulative energies or functions thereof and using said values to yield a measure of the gemstone's proportion.

15. The non-transitory computer readable memory of claim 13, wherein spatially separating comprises filtering or weighted transformation of said datasets.

16. The non-transitory computer readable memory of claim 10, wherein said simulated electromagnetic waves comprise light emitted from simulated illumination sources.

17. The non-transitory computer readable memory of claim 10, wherein said predetermined surface, comprises any one of the following:

the gemstone surface,
a spherical surface centered at a girdle center of the gemstone,
a spherical surface centered at a table center of the gemstone,
a far field surface for the simulated electromagnetic waves.

18. The non-transitory computer readable memory of claim 10, wherein the dataset is representative of locations on the predetermined surface where the energy is distributed.

* * * * *